US012599425B2

(12) United States Patent
Jeong et al.

(10) Patent No.: US 12,599,425 B2
(45) Date of Patent: *Apr. 14, 2026

(54) SYSTEMS FOR PERIVASCULAR NERVE DENERVATION

(71) Applicant: DeepQure Inc., Seoul (KR)

(72) Inventors: Chang Wook Jeong, Seoul (KR); Seok Joo Chang, Seoul (KR); Du Jin Bach, Seongnam-si (KR)

(73) Assignee: DEEPQURE INC., Seoul (KR)

( * ) Notice: Subject to any disclaimer, the term of this patent is extended or adjusted under 35 U.S.C. 154(b) by 1208 days.

This patent is subject to a terminal disclaimer.

(21) Appl. No.: 17/113,935

(22) Filed: Dec. 7, 2020

(65) Prior Publication Data

US 2021/0085382 A1 Mar. 25, 2021

Related U.S. Application Data

(63) Continuation-in-part of application No. 16/239,718, filed on Jan. 4, 2019, which is a continuation-in-part
(Continued)

(51) Int. Cl.
*A61B 18/14* (2006.01)
*A61B 17/32* (2006.01)
(Continued)

(52) U.S. Cl.
CPC .... *A61B 18/082* (2013.01); *A61B 17/320068* (2013.01); *A61B 18/02* (2013.01);
(Continued)

(58) Field of Classification Search
CPC ...... A61B 2018/142; A61B 2018/1467; A61B 5/6877; A61B 2562/164; A61B 2562/166; A61B 5/294
See application file for complete search history.

(56) References Cited

U.S. PATENT DOCUMENTS 3,955,578 A 5/1976 Chamness et al.
5,433,708 A 7/1995 Nichols et al.
(Continued)

FOREIGN PATENT DOCUMENTS

KR 10-1370048 B1 2/2014
KR 10-1399555 B1 5/2014

OTHER PUBLICATIONS

Applicant hereby advises the Examiner of the status of co-pending applications in compliance with the Applicant's duty to disclose under 37 C.F.R. §§ 1.56 and 1.2 (see also MPEP § 2001.06(b)) as discussed in *McKesson Info. Soln. Inc.*, v. *Bridge Medical Inc.*, 487 F.3d 897; 82 USPQ2d 1865 (Fed. Cir. 2007).
(Continued)

*Primary Examiner* — Jaymi E Della
(74) *Attorney, Agent, or Firm* — Merchant & Gould P.C.

(57) ABSTRACT

Provided is a catheter including a shaft having a distal end and a loop disposed near the distal end and configured to curl around a tissue and receive, via the shaft, energy to denervate at least a portion of the tissue. The loop includes: a first film capable of bending to curl around the tissue; a plurality of electrodes disposed on the first film and arranged in parallel to each other with a predetermined distance; a sensor disposed at a position corresponding to a position between the plurality of electrodes.

13 Claims, 27 Drawing Sheets

Related U.S. Application Data of application No. 15/258,167, filed on Sep. 7, 2016, now Pat. No. 11,259,859.

(51) Int. Cl.

| | |
|---|---|
| *A61B 18/02* | (2006.01) |
| *A61B 18/08* | (2006.01) |
| *A61B 18/24* | (2006.01) |
| *A61B 18/00* | (2006.01) |
| *A61B 18/12* | (2006.01) |

(52) U.S. Cl.

CPC .......... *A61B 18/1492* (2013.01); *A61B 18/24* (2013.01); *A61B 2018/00083* (2013.01); *A61B 2018/00184* (2013.01); *A61B 2018/00345* (2013.01); *A61B 2018/00434* (2013.01); *A61B 2018/00511* (2013.01); *A61B 2018/00791* (2013.01); *A61B 2018/00875* (2013.01); *A61B 2018/0212* (2013.01); *A61B 2018/126* (2013.01); *A61B 2018/1407* (2013.01); *A61B 2018/142* (2013.01); *A61B 2018/1467* (2013.01); *A61B 2018/1475* (2013.01)

(56) References Cited

U.S. PATENT DOCUMENTS

| | | | |
|---|---|---|---|
| 5,486,183 A | 1/1996 | Middleman et al. | |
| 5,520,684 A | 5/1996 | Imran | |
| 6,050,995 A | 4/2000 | Durgin | |
| 6,162,184 A | 12/2000 | Swanson et al. | |
| 6,595,991 B2 | 7/2003 | Töllner et al. | |
| 6,978,174 B2 | 12/2005 | Gelfand et al. | |
| 8,150,520 B2 | 4/2012 | Demarais et al. | |
| 8,473,067 B2 | 6/2013 | Hastings et al. | |
| 8,740,849 B1 | 6/2014 | Fischell et al. | |
| 2003/0018330 A1 | 1/2003 | Swanson et al. | |
| 2004/0193151 A1 | 9/2004 | To et al. | |
| 2005/0015083 A1 | 1/2005 | Koblish et al. | |
| 2006/0009759 A1 | 1/2006 | Chrisitian et al. | |
| 2006/0030919 A1* | 2/2006 | Mrva ................... | A61N 1/0556 607/118 |
| 2006/0041277 A1 | 2/2006 | Deem et al. | |
| 2010/0137860 A1 | 6/2010 | Demarais et al. | |
| 2010/0168739 A1 | 7/2010 | Wu et al. | |
| 2011/0112400 A1 | 5/2011 | Emery et al. | |
| 2012/0197246 A1 | 8/2012 | Mauch | |
| 2012/0259269 A1 | 10/2012 | Meyer | |
| 2013/0150940 A1* | 6/2013 | Wilson ................. | A61B 5/4094 607/118 |
| 2014/0018788 A1 | 1/2014 | Engelman et al. | |
| 2014/0107639 A1 | 4/2014 | Zhang et al. | |
| 2014/0303618 A1 | 10/2014 | Wu et al. | |
| 2015/0025524 A1 | 1/2015 | Nabutovsky | |
| 2015/0119882 A1* | 4/2015 | Cao .................... | A61B 18/1492 606/41 |
| 2015/0141810 A1 | 5/2015 | Weadock | |
| 2015/0224326 A1* | 8/2015 | Toth ........................ | A61B 7/04 600/377 |
| 2015/0224356 A1 | 8/2015 | Holland et al. | |
| 2016/0089198 A1 | 3/2016 | Arya et al. | |
| 2016/0113711 A1 | 4/2016 | Osypka et al. | |
| 2016/0143642 A1 | 5/2016 | Wright | |
| 2016/0256218 A1* | 9/2016 | Gandhi ............. | A61B 18/1206 |
| 2017/0202467 A1 | 7/2017 | Zitnik et al. | |
| 2018/0318578 A1* | 11/2018 | Ng ........................ | A61B 5/4818 |
| 2019/0059820 A1* | 2/2019 | Schuettler ........... | A61N 1/0556 |
| 2019/0076583 A1 | 3/2019 | Kim | |

OTHER PUBLICATIONS

The Applicant wishes to bring to the Examiner's attention U.S. Appl. No. 15/258,167, filed Sep. 7, 2016, which is now granted as U.S. Pat. No. 11,259,859.

The Applicant wishes to bring to the Examiner's attention U.S. Appl. No. 17/012,534, filed Sep. 4, 2020, which is now pending.

The Applicant wishes to bring to the Examiner's attention U.S. Appl. No. 16/239,718, filed Jan. 4, 2019, which is now pending.

The Applicant wishes to bring to the Examiner's attention U.S. Appl. No. 17/195,011, filed Mar. 8, 2021, which is now pending.

The Applicant wishes to bring to the Examiner's attention U.S. Appl. No. 17/190,161, filed Mar. 2, 2021, which is now pending.

The Applicant wishes to bring to the Examiner's attention U.S. Appl. No. 17/375,359, filed Jul. 14, 2021, which is now pending.

The Applicant wishes to bring to the Examiner's attention U.S. Appl. No. 17/190,183, filed Mar. 2, 2021, which is now pending.

Office Action issued for U.S. Appl. No. 15/258,167, filed Jun. 3, 2019, 12 pages.

Baik, Jinhwan et al. "Laparoscopic Renal Nerve Denervation System for Treating Resisant Hypertension: Overcoming Limitations of Catheter-based Approaches", DOI 10.1109/TBME.2020.2987531, IEEE Transactions on Biomedical Engineering (vol. 67, Issue: 12, Dec. 2020), 12 pages.

* cited by examiner

<u>300</u>

900

SYSTEMS FOR PERIVASCULAR NERVE DENERVATION

CROSS-REFERENCE TO RELATED APPLICATION

This application is a continuation-in-part of U.S. patent application Ser. No. 16/239,718 filed on Jan. 4, 2019 and U.S. patent application Ser. No. 15/258,167 filed on Sep. 7, 2016, which are incorporated herein by reference in their entirety.

STATEMENT REGARDING PRIOR DISCLOSURES BY THE INVENTOR OR A JOINT INVENTOR

This Application is a continuation-in-part of U.S. patent application Ser. No. 16/239,718 filed on Jan. 4, 2019 (abandoned) and U.S. patent application Ser. No. 15/258,167 filed on Sep. 7, 2016 (U.S. Pat. No. 11,259,859), which are incorporated herein by reference in their entirety.

FIELD OF THE INVENTION

The present disclosure relates to perivascular nerve 10 denervation in an autonomic nerve system, and more particularly to catheter apparatus for perivascular nerve denervation to reduce a nerve activity.

BACKGROUND

High blood pressure is often difficult to control. Resistant hypertension is defined as a blood pressure that remains above goal despite the concomitant use of full doses of three or more antihypertensive drugs from different classes. One approach to treat patients with resistant hypertension is renal denervation for blocking sympathetic nerve around the renal artery of the patients.

Recently, it has been reported that renal denervation for blocking sympathetic nerve around the renal artery using percutaneous catheter can be effective for lowering blood pressure in patients with resistant hypertension. Besides, this renal denervation strategy has gained attention for the usefulness in the treatment of patients with arrhythmia and cardiac failure.

However, in the existing approaches for performing renal denervation, it is difficult to destruct effectively renal nerves since most of the renal nerves are distributed far away from the intima of renal artery and the conventional percutaneous catheters are designed to destruct the renal nerves from inner side of the renal artery. Also, the conventional percutaneous catheters may severely damage the intima of the renal artery as well as the adventitia of the renal artery and, in some cases, may cause angiostenosis.

Therefore, there is a need for new catheters that can help the physicians effectively destruct the renal nerves for performing renal denervation without damaging the renal artery and nearby organs/tissues.

SUMMARY OF THE INVENTION

The present disclosure provides a catheter apparatus for perivascular nerve denervation that effectively and completely destruct a circumferential tissue of vascular (e.g., artery), such as renal artery nerves, hepatic artery nerves, splenic artery nerves and pulmonary artery nerves.

In accordance with an aspect of the present disclosure, the catheter apparatus for perivascular nerve denervation includes: a shaft having a distal end; and a loop disposed near the distal end and configured to curl around a tissue and receive, via the shaft, energy to denervate at least a portion of the tissue, wherein the loop includes: a first film capable of bending to curl around the tissue; a plurality of electrodes disposed on the first film and arranged in parallel to each other with a predetermined distance; a sensor disposed at a position corresponding to a position between the plurality of electrodes.

The plurality of electrodes include a first electrode to deliver thermal energy to a first treatment zone of the tissue and a second electrode to deliver thermal energy to a second treatment zone of the tissue.

Thermal energy delivered to the plurality of electrodes is localized between the first treatment zone and the second treatment zone.

The plurality of electrodes are configured to form a bipolar configuration to localize the thermal energy.

The loop is configured to curl to contact the tissue.

The plurality of electrodes are configured to curl to directly or indirectly contact the tissue.

The loop further includes a second film on which the first film is disposed.

The sensor is disposed on the second film.

The first film is a polyimide film, and the second film is a biocompatible heat-treated stainless steel plate.

The second film is coated with a flexible printed circuit board.

The loop further includes a third film on which the second film is disposed.

The energy received by the loop is at least one selected from the group consisting of radio-frequency (RF) energy, electrical energy, laser energy, ultrasonic energy, high-intensity focused ultrasound (HIFU) energy, cryogenic energy, thermal energy.

The sensor is electrically insulated from the plurality of electrodes and sense at least one of an impedance of the plurality of electrodes and a temperature of the tissue.

The tissue includes at least one of a nerve, lymphatics and capillaries around an artery.

BRIEF DESCRIPTION OF THE DRAWINGS

The objects, features and advantages of the present disclosure will be more apparent from the following detailed description in conjunction with the accompanying drawings, in which.

DETAILED DESCRIPTION OF EXEMPLARY EMBODIMENTS

Figure 1:
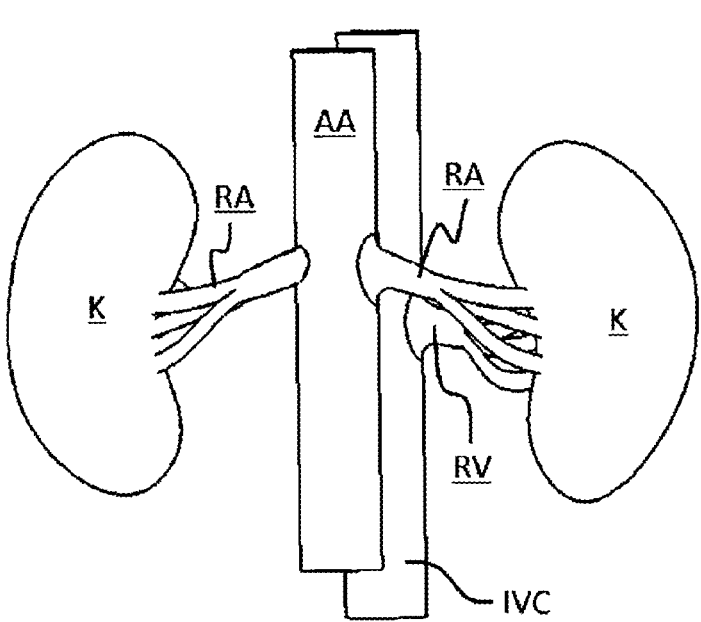
FIG. 1 illustrates anatomy of a human kidney.

Exemplary embodiments of the present disclosure are described with reference to the accompanying drawings in detail. The same reference numbers are used throughout the drawings to refer to the same or like parts. Detailed descriptions of well-known functions and structures incorporated herein may be omitted to avoid obscuring the subject matter of the present disclosure.

Components, or nodes, shown in diagrams are illustrative of exemplary embodiments of the invention and are meant to avoid obscuring the invention. It shall also be understood that throughout this discussion that components may be described as separate functional units, which may comprise sub-units, but those skilled in the art will recognize that various components, or portions thereof, may be divided into separate components or may be integrated together, including integrated within a single system or component.

Reference in the specification to "one embodiment," "preferred embodiment," "an embodiment," or "embodiments" means that a particular feature, structure, characteristic, or function described in connection with the embodiment is included in at least one embodiment of the invention and may be in more than one embodiment. The appearances of the phrases "in one embodiment," "in an embodiment," or "in embodiments" in various places in the specification are not necessarily all referring to the same embodiment or embodiments.

The terms and words used in the following description and claims are not limited to the bibliographical meanings, but, are merely used by the inventor to enable a clear and consistent understanding of the present disclosure.

In the present disclosure, the terms such as "include" and/or "have" may be construed to denote a certain characteristic, number, step, operation, constituent element, component or a combination thereof, but may not be construed to exclude the existence of or a possibility of addition of one or more other characteristics, numbers, steps, operations, constituent elements, components or combinations thereof.

Several embodiments of the present disclosure described herein relate generally to apparatus, systems and methods for therapeutically effecting neuromodulation (e.g., nerve disruption, nerve denervation, nerve stimulation) of target nerve to treat various medical conditions, disorders and diseases. In embodiments, neuromodulation of the target nerve may be used to treat or reduce the risk of occurrence of symptoms associated with a variety of metabolic diseases. For example, neuromodulation of the target nerve may treat or reduce the risk of occurrence of symptoms associated with hypertension or other hypertension-related diseases, diabetes or other diabetes-related disease. If human patient has a vascular diseases, such as hypertension, the methods described herein may advantageously treat hypertension without taking hypertension drugs and if human patient has diabetes mellitus, the methods described herein may advantageously treat diabetes without requiring daily insulin injection or constant monitoring of blood glucose levels. The treatment provided by the apparatus, systems and methods described herein may be permanent or at least semi-permanent, thereby reducing the need for continued or periodic treatment.

In embodiments, neuromodulation of the target nerve as described herein may be used for the treatment of insulin resistance, genetic metabolic syndromes, ventricular tachycardia, atrial fibrillation or flutter, arrhythmia, inflammatory diseases, hypertension, obesity, hyperglycemia, hyperlipidemia, eating disorders, and/or endocrine diseases.

The neuromodulation of the target nerve is not limited to the disease treatment described above and can be used to treat other suitable types of diseases that one skilled in the art appreciates or recognizes.

FIG. 1 illustrates a common human renal anatomy. As depicted, the kidneys K are supplied with oxygenated blood by renal arteries RA, which are connected to the heart by the abdominal aorta AA. Deoxygenated blood flows from the kidneys to the heart via renal veins RV and the inferior vena cava IVC.

Figure 2A:
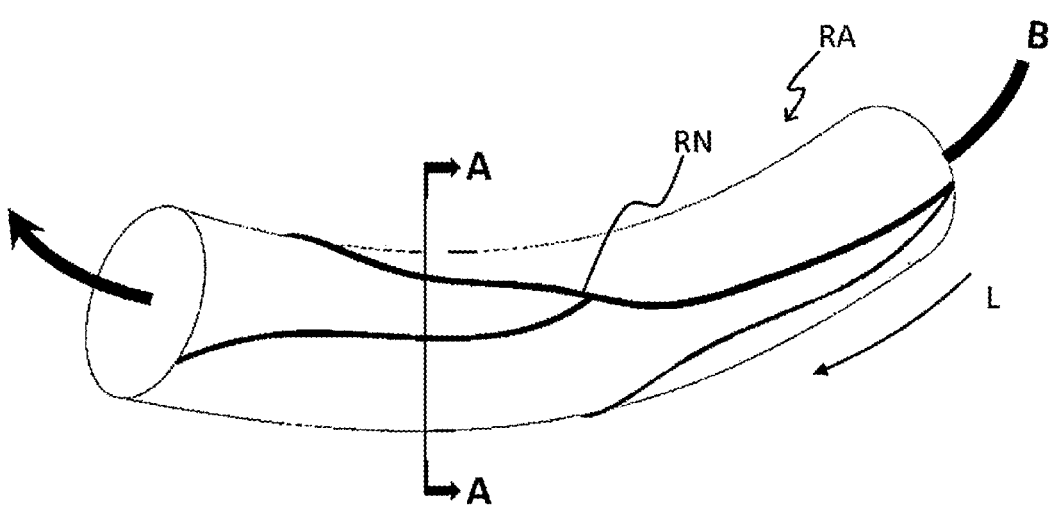
FIG. 2A is a schematic diagram of human renal nerves and renal artery.
Figure 2B:
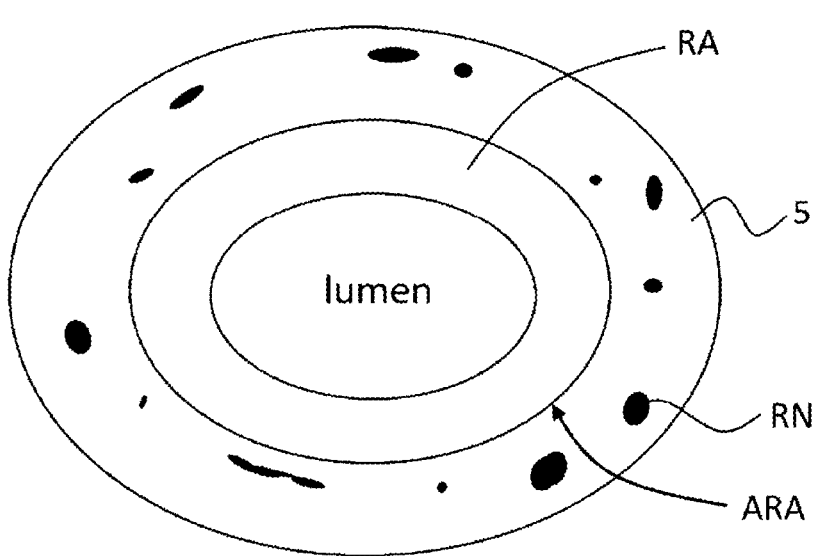
FIG. 2B is a cross sectional view of human renal artery and renal nerves.

FIG. 2A illustrates a portion of human renal artery RA and renal nerves RN. FIG. 2B illustrates a cross-sectional view taken along the radial plane A-A of FIG. 2A.

As depicted, the renal artery RA has a lumen through which the blood B flows. The renal nerves RN are located in proximity to the adventitia of the renal artery ARA and run along the renal artery RA in a lengthwise direction L. More specifically, renal nerves RN are situated in a circumferential tissue 5 surrounding the outer wall of the renal artery RA and the circumferential tissue 5 may include other tissue, such as lymphatics and capillaries.

In the conventional approaches based on applying denervation energy to destroy the renal nerves RN, a catheter is inserted into the lumen and delivers heat energy to denervate the target renal nerves RN. During this process, the denervation energy may damage the adventitia ARA of renal artery RA before it reaches the renal nerves RN. Furthermore, a portion of the denervation energy may be absorbed by the adventitia of the renal artery ARA, reducing the efficiency in utilizing the energy. Accordingly, it may be more effective and safer to denervate from outside of the renal artery RA (i.e., apply energy from outside of RA) than to denervate from inside of the renal artery RA (i.e., apply energy from inside of RA).

Figure 3:
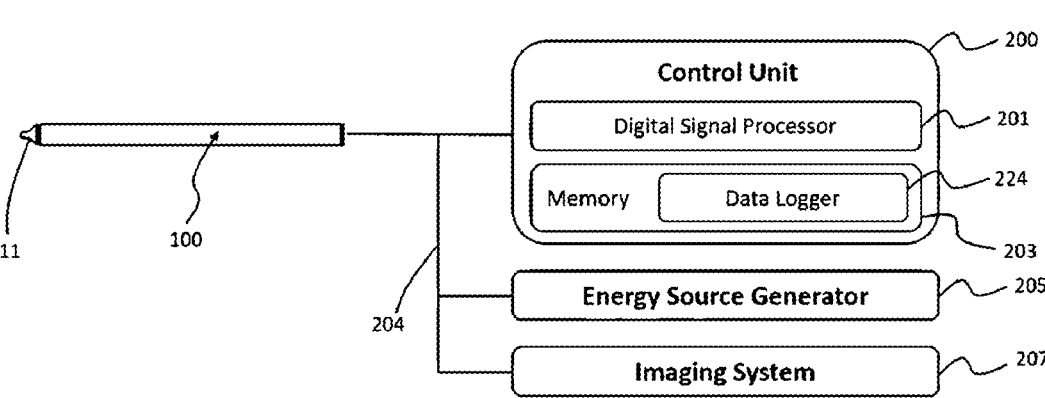
FIG. 3 is a schematic block diagram of a catheter system for renal denervation according to embodiments of the present invention.

FIG. 3 is a schematic block diagram of a catheter system 300 for renal denervation according to embodiments of the present invention. As depicted, the catheter system 300 includes: a catheter apparatus 100 having a distal portion 11 which may make a contact with a target tissue and/or be disposed in proximity to the target tissue for treatment; a control unit 200 for controlling one or more components of the system 300; an energy source generator (ESG) 205 for supplying energy to the target tissue through the distal portion 11 of the catheter apparatus 100; an imaging system 207 for processing visual images and displaying the images to the users; and wires/cables/buses 204 that connect the components of the system 300 to each other for communication. In the present disclosure, the target tissue is described as the renal artery nerves, but it should be apparent to those of ordinary skill in the art that the target tissue means various artery nerves, such as renal artery nerves, hepatic artery nerves, splenic artery nerves and pulmonary artery nerves The control unit 200 may collectively refer to one or more components for controlling various components of the catheter system 300. In embodiments, the control unit 200 may include a digital signal processor (DSP) 201, such as CPU, and a memory 203. The memory 203 may store various data and include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices.

In embodiments, a data logger 224 may be included in the memory 203 and store data (e.g., temperature of the target tissue) measured by the catheter 100 during the denervation procedure. It is note that the memory 203 may be located outside the control unit 200 and coupled to the control unit 200 via a wire/cable 204.

It is noted that the control unit 200 may be a computer, a server, or any other suitable computing facility and include other components, such as printer, input device (such as keyboard and mouse), scanner, display device, and a network interface.

In embodiments, the distal portion 11 may include denervation element(s) and optionally an endoscope or some other type of imaging device, coupled to an imaging system 207, to provide images of the target tissue using suitable imaging techniques. The imaging device may allow the operator/physician to visually identify the region being ablated/denervated, to monitor the progress of the ablation/denervation in real time, and to address safety concerns during operation.

Figure 4:
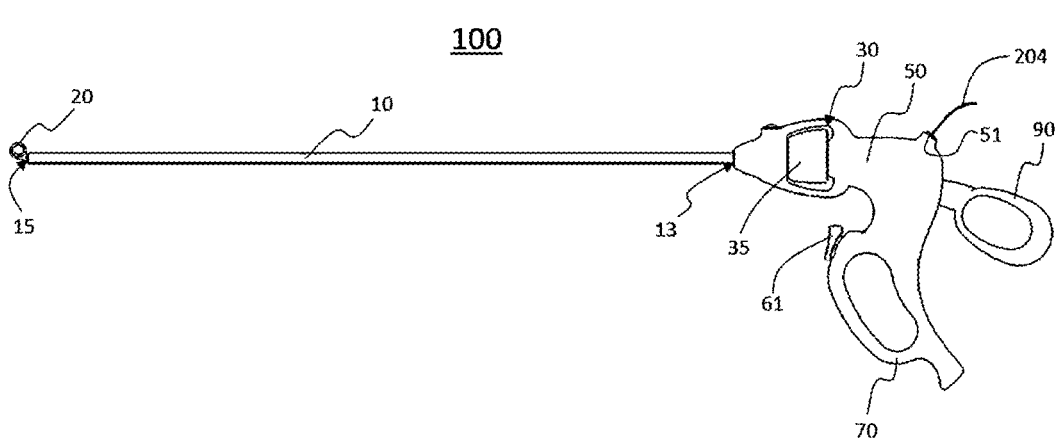
FIG. 4 is a side elevational view of a catheter according to embodiments of the present invention.

FIG. 4 is a side elevational view of a catheter apparatus 100 according to embodiments of the present invention. As depicted, the catheter apparatus 100 comprises a shaft 10, a loop 20, a holder 30, a slider 35, a butt 50, a handle 70 and a loop control 90.

The shaft 10 has a proximal end 13 coupled to the holder 30 and a distal end 15 removably connected to the distal portion 11 of the catheter apparatus 100. The shaft 10 has a shape of tube, forming a channel that extends from the proximal end 13 to the distal end 15, and is dimensioned to allow a stylet and/or a wire(s) to pass therethrough. The distal portion 11 may form a passage through which the loop 20 travels, as explained in detail below.

In embodiments, the shaft 10 may be made of silicone, polyurethane (PU), Pebax, or a combination of PU and silicone, or some other biocompatible polymers and/or metallic materials. The shaft 10 may be sufficiently large enough to house an imaging device, such as an endoscope, as well as components for ablation/denervation. In embodiments, the shaft 10 may include electrical wires/cables that run from the energy source generator 204 to the electrodes on the loop 20. In embodiments, the shaft 10 may include wires/cables for providing electrical energy to the endoscope and transmitting visual images from the endoscope to the control unit 200. In embodiments, the shaft 10 may be dimensioned to provide safe and easy treatment of the target tissue with minimal percutaneous access site on the patient, for example, on the abdominal region.

In embodiments, the loop 20 may be removably coupled to the distal end 15 of the shaft 10 and mechanically connected to the shaft 10.

The holder 30 is connected to the proximal end 13 of the shaft 10. More specifically, the holder 30 may have a structure for accepting the proximal end 13 of the shaft 10 therein and be electrically coupled to the proximal end 13. In embodiments, a slider 35 may be rotatably coupled to the holder 30 and the operator may rotate the slider 35 to engage (or disengage) the shaft 10 to (or from) the holder 30.

In embodiments, the holder 30 may include the butt 50 and a terminal 51 disposed on one side of the butt 50. The terminal 51 may receive various types of energy from the energy source generator 205 via the wire/cable 204 and the energy is delivered from the terminal 51 to the loop 20 via suitable wires/cables running through the shaft 10. In embodiments, the energy may be, but not limited to, at least one of a radio-frequency (RF) energy, electrical energy, laser energy, ultrasonic energy, high-intensity focused ultrasound (HIFU) energy, cryogenic energy, and thermal energy. Energy may be delivered to the loop 20, simultaneously or sequentially, or selectively. For selective delivery, a clinician can select, via a user interface of the energy source generator 205, such as an RF generator, a specific electrode to be utilized in the denervation process, where the electrode is disposed in the loop 20.

The handle 70 may extend from the butt 50. The handle may have a vacant space (hole) into which the operator may insert his finger(s) to have a firm grip of the holder 30.

A push-button 61 may be disposed on another side of the butt 50 or one side of the handle 70. The push-button 61 is operated by the operator to control the energy flow to the loop 20.

The loop control 90 may be hinged on the butt 50 or the handle 70. The loop control 90 may also have a vacant space (hole) in which the operator's thumb can be inserted. As described below, the operator may control the loop control 90 to coil/uncoil the loop 20.

Figure 5:
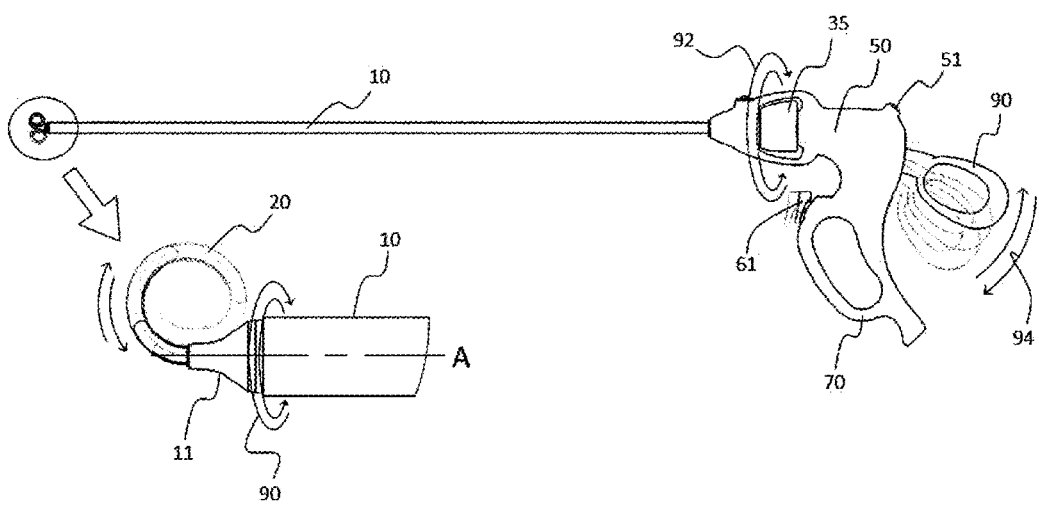
FIG. 5 illustrates an exemplary operation of a catheter according to embodiments of the present invention.
Figure 6A:
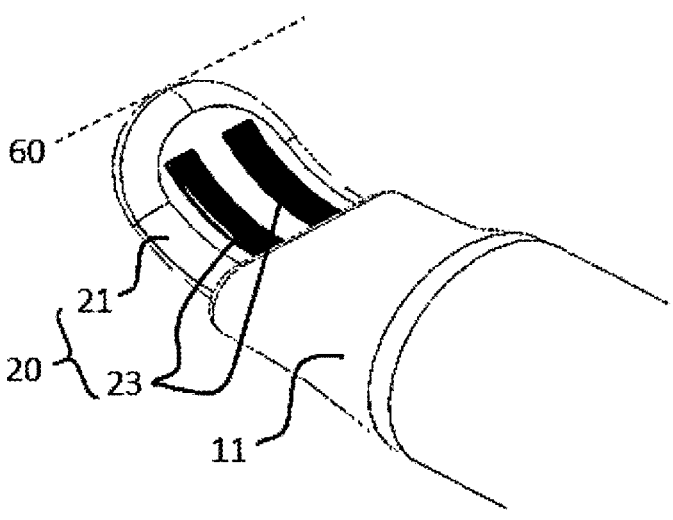
FIG. 6A to 6D and FIG. 7A to 7D illustrate loops of the catheter in FIG. 4 according to embodiments of the present invention.
Figure 6B:
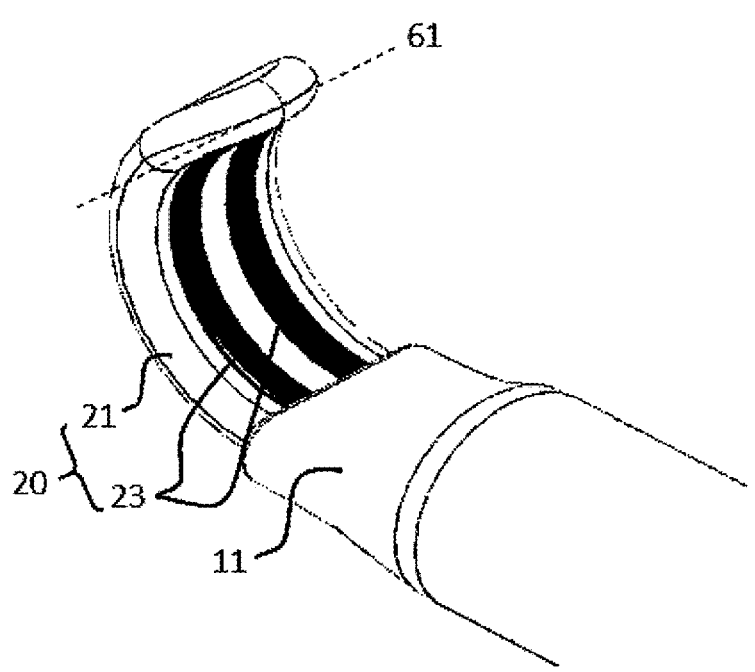
Figure 6C:
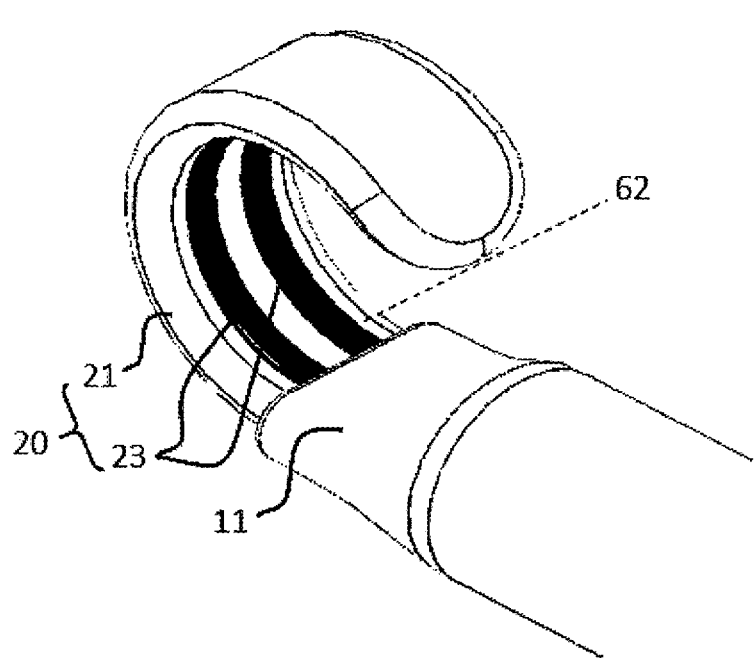
Figure 6D:
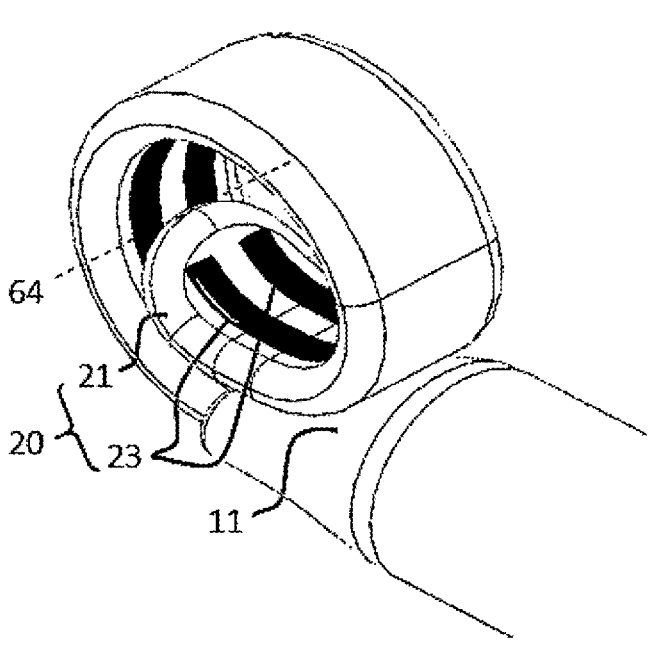
Figure 7A:
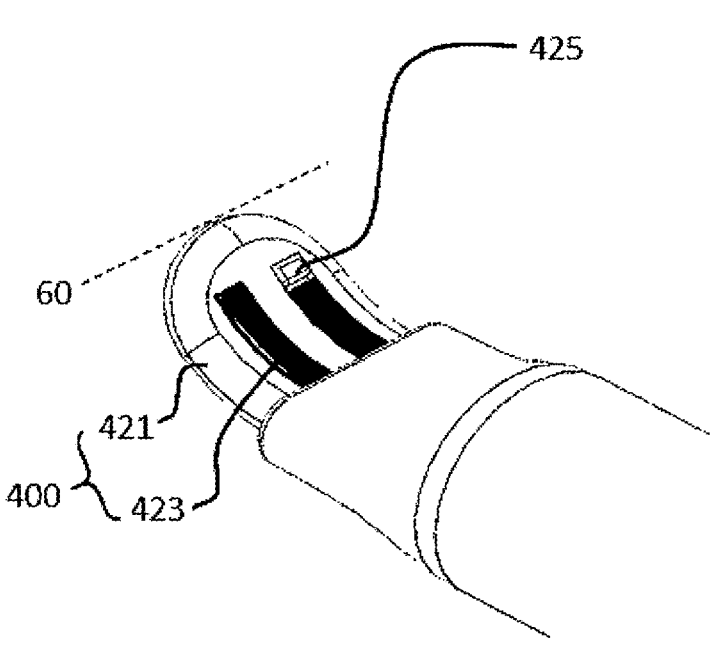
Figure 7B:
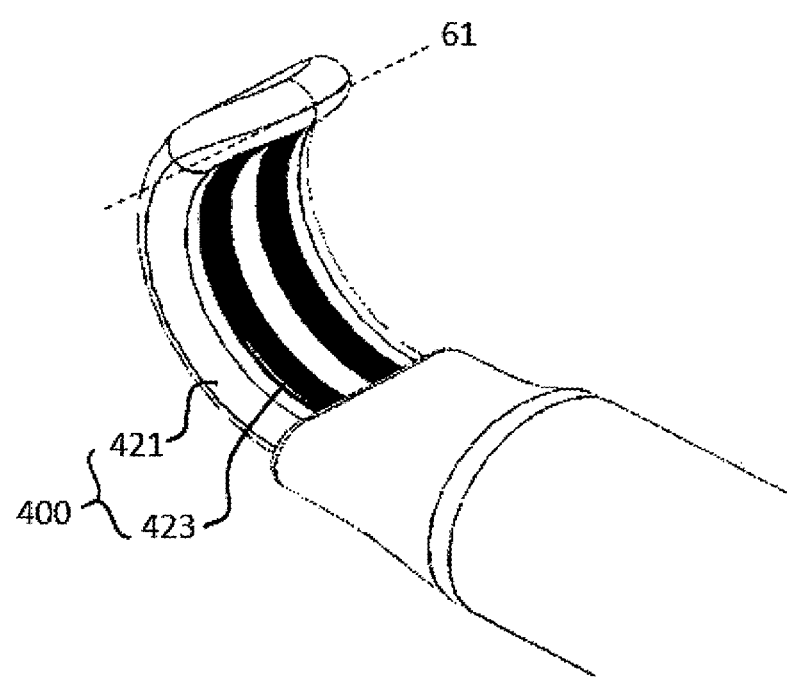
Figure 7C:
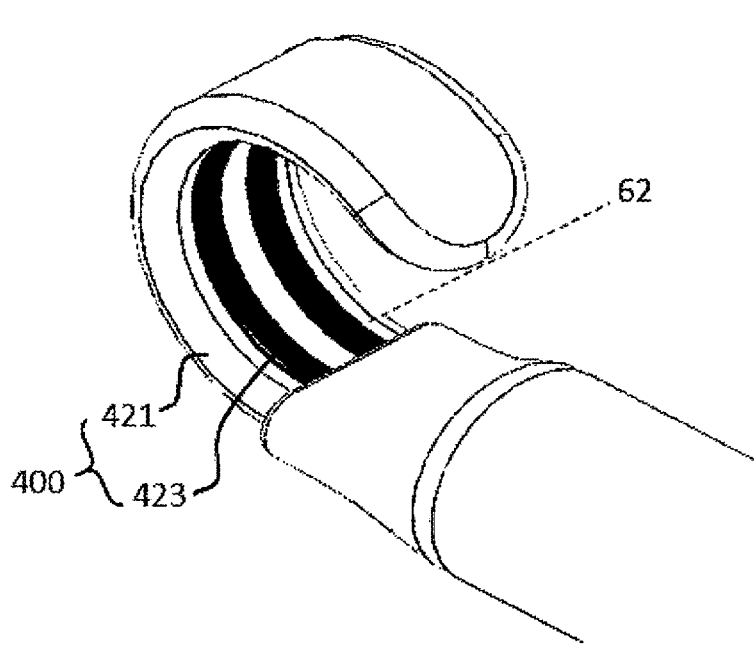
Figure 7D:
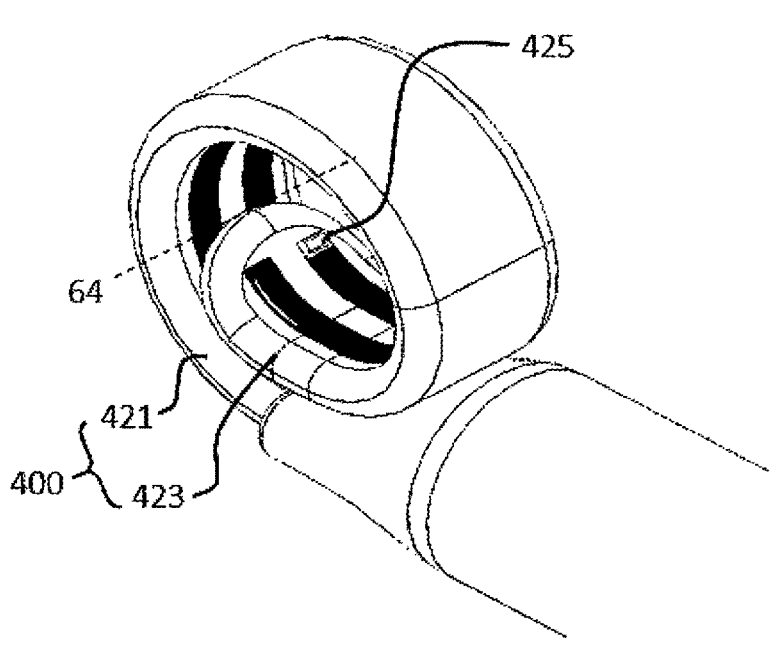

FIG. 5 illustrates an example of an operation of a catheter according to an embodiment of the present invention. As shown in the FIG. 5, the slider 35 may be rotated up to about 360 degrees about the longitudinal axis A of the shaft 10. A rotational direction of the slider 35 may be bidirectional or unidirectional. As the slider 35 rotates, as indicated by the arrows 92, the loop 20 may also rotate around the longitudinal axis A of the shaft 10, as indicated by the arrows 90. Thus, a rotation of the loop 20 about the longitudinal axis of the shaft 10 may be controlled by the rotation of the slider 35.

In embodiments, when moved forward/backward (or upward/downward) by the operator's finger, as indicated by arrows 94, the loop control 90 mechanically controls the loop 20, where the loop control 90 may be designed to operate in various modes. In one mode, as the loop control 90 moves forward (or downward), the loop 20, which is originally rolled, may be unrolled to a straight segment and extend along the longitudinal axis A of the shaft 10. As the loop control 90 moves backward (or upward), the loop 20 is rolled to its original shape. In this mode, the operator may bring the loop 20 near the target tissue or renal artery RA and move the loop control 90 backward to curl the loop 20 around the target tissue or renal artery RA.

In another mode, the loop 20 may be retracted into the shaft 10. As the loop control 90 is moved forward (or downward), the loop 20 may emerge from the distal portion 11 and become a straight segment or curl into a semi-circle. As the loop control 90 is moved backward (or upward), the loop 20 may curl around the target tissue or renal artery RA.

FIG. 6A to FIG. 6D show a loop that curls as it emerges from the shaft 10 of the catheter apparatus according to embodiments of the present invention. As depicted, the loop 20 includes a body 21 and one or more electrodes 23 disposed on the body 21. The loop 20 may remain inside the shaft 10 and distal portion 11 (retracted position) when the loop control 90 is in the neutral position. As the operator moves the loop control 90 forward (or downward), the loop emerges from the distal portion 11, forming a curved segment. As depicted in FIG. 6A to 6D, the loop 20 curls as the tip of the loop 20 proceeds from the position 60 toward the position 64.

In embodiments, the body 21 may be made of a flexible material. In embodiments, the body 21 may be made of thermally non-conductive elastic material so that the energy delivered to the electrodes 23 is localized only to a portion(s) of the tissue that the electrodes 23 contact. As the localized energy is used to denervate the renal nerves RN (shown in FIG. 3), the potential damage caused by the loop 20 to the tissue nearby the renal nerves RN may be significantly reduced during operation.

Figure 8:
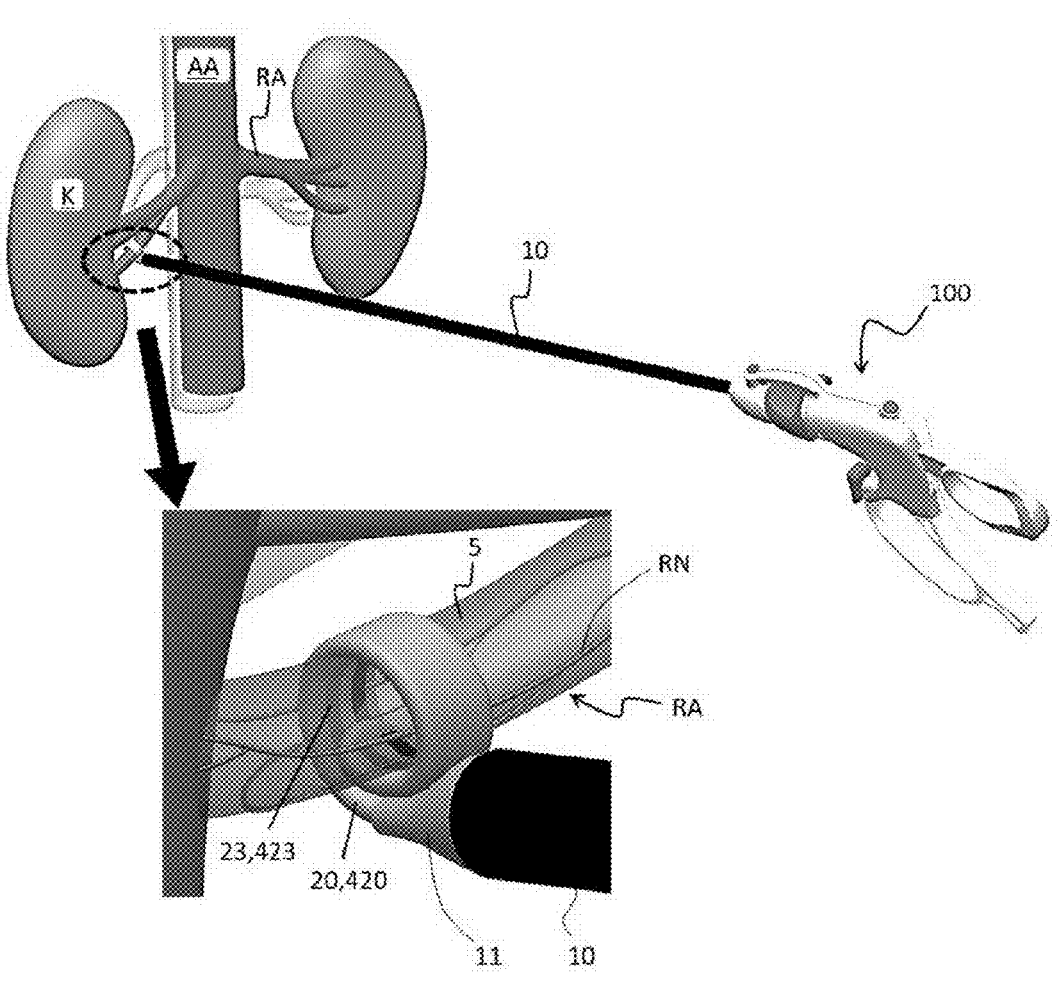
FIG. 8 is a schematic diagram of a catheter, illustrating renal denervation using the catheter according to embodiments of the present invention.

In embodiments, the loop 20 may be flexible and deformable to curl around a renal artery as discussed in conjunction with FIG. 8. The loop 20 may be designed for two different operational modes. In the first mode, the loop 20 may remain flat when the loop 20 is brought into proximity to the target tissue, such as the circumferential tissue 5 of the renal artery. Then, the operator may manipulate the loop control 90 to curl the loop 20 around the circumferential tissue 5 and perform denervation. Upon completing the denervation, the operator may release the loop control 90 to uncurl loop 20. In the second mode, the loop 20 may remain curled when the distal portion 11 is brought into proximity to the target tissue. Then, the operator may manipulate the loop control 90 to uncurl the loop 20, position the loop 20 around the target tissue, release the loop control 90 to curl the loop 20 around the renal artery and perform denervation.

In embodiments, the electrodes 23 may be disposed on the inner side of the body 21 so that the electrodes 23 may contact the circumferential tissue 5 when the loop 20 curls around the circumferential tissue 5. In embodiments, the electrodes 23 may extend along the longitudinal direction of the body 21 and be arranged in parallel to each other. In one embodiment, the body 21 may be formed of dielectric material and the electrodes 23 may be formed on the inner surface of the body 21. In embodiments, the body 21 may have a groove or a channel on the inner surface of the body 21 and the electrodes 23 may be formed by filling electrically conductive material in the groove or the channel.

In another embodiment, the body 21 may be formed of electrically conducting material and the entire surface of the body 21 may be covered with dielectric material except the location where the electrodes 23 are to be located. In embodiments, a dielectric body may be disposed between the two electrodes 23 to electrically isolate the electrodes 23 from each other.

In embodiments, the electrodes 23 may be formed of electrically-conductive elastic material so that they can deform along with the body 21 as the body 21 is curled/uncurled. In embodiments, the electrodes 23 may contact the circumferential tissue 5 surrounding the outer surface of the renal artery and generate heat energy when electrical energy, such as RF energy, is supplied, where the heat energy may be used to denervate the renal nerve RN.

In FIG. 6A to 6D, only two electrodes 23 are shown. However, it should be apparent to those of ordinary skill in the art that any suitable number of electrodes may be used. For instance, if the electrical energy is supplied as unipolar energy, a single electrode may be used. In another example, if the electrical energy is supplied as bipolar energy, two or more electrodes may be used.

FIG. 7A to 7D show a loop 400 according to embodiments of the present invention. As depicted, the loop 400 is similar to the loop 20, with the difference that a sensor 425 is mounted to the body 421. In embodiments, the sensor 425 and the electrodes 423 may be disposed on the inner side of the body 421.

In embodiments, the sensor 425 may be mounted in the body 421 formed of dielectric material so that the sensor 425 may be electrically insulated from the electrode 423. The electrodes 423 and sensor 425 may move along the body 421 when the loop 420 curls/uncurls around the target tissue.

When the electrode(s) 423 and the sensor 425 curl around the circumferential tissue 5 of the renal artery, in embodiments, the electrode(s) 423 and the sensor 425 contact the circumferential tissue 5. For instance, the electrode(s) 423 may receive electrical energy such as RF energy and generate heat energy. The sensor 225 may measure the impedance of the electrodes 423 or the temperature of the circumferential tissue. The sensor 425 may be connected to the central controller 200 via a wire(s) that run through the catheter apparatus 100, where electrical power for the sensor 425 may be also delivered via a wire(s).

Information of the measured impedance or temperature may be transmitted to the memory 203 of the catheter system 300. In embodiments, the operator may diagnose the denervation process using the information. The power for delivering thermal energy may also be automatically controlled by the energy source generator 205 or the central controller 200 based on the information. It is noted that other types of sensor may be used to measure various quantities, where each quantity may indicate the status of the denervation process and provide guidance to the physician during operation.

FIG. 8 is a schematic diagram of a catheter, illustrating renal denervation using the catheter according to embodiments of the present invention As shown in FIG. 8, the distal portion 11 of the catheter is advanced into proximity of the patient's renal artery RA. The operator may operate the loop control 90 so that the loop 20 (or 420) including a plurality of electrodes 23 (or 423) may curl around the circumferential tissue 5 of the renal artery to thereby directly or indirectly contact the circumferential tissue of the renal artery RA. The electrodes 23 (or 423) may be positioned on a circumferential treatment zone along a segment of the renal artery RA. The electrodes 23 (or 423) may include a first electrode to deliver thermal energy to a first treatment zone of the renal artery RA a second electrode to deliver thermal energy to a second treatment zone of the renal artery RA.

In embodiments, each of the electrodes may deliver thermal energy to a different treatment zone, respectively or deliver thermal energy to the same treatment zone.

In embodiments, the loop 20 (or 420) may be electrically coupled to energy source generator 205 for delivery of a desired electrical energy to the electrodes (or 423). In embodiments, the electrical energy may be thermal RF energy using Quantum Molecular Resonance (QMR). A frequency of the RF energy may be higher than or equal to 4 MHz and may destruct at least a portion of the circumferential tissue 5 of the renal artery RA. In embodiments, the temperature range of the electrodes 23 (or 423) during operation ranges from 60 degrees to 70 degrees.

In embodiments, the loop 20 (or 420) may supply electrical energy to the circumferential tissue 5 of the renal artery RA to cause renal denervation through the electrode 23 (or 423). The heat energy, which is generated by the electrodes 23 (423), may destruct a portion of the circumferential tissue of the renal artery, where the circumferential tissue may include at least one of a renal nerve RN, lymphatics and capillaries. This may be achieved via contact between the loop 20 (or 420) and the circumferential tissue 5 of the renal artery RA. In embodiments, during the denervation, an impedance of the electrode or a temperature of the circumferential tissue may be measured using the sensor 425.

Figure 9:
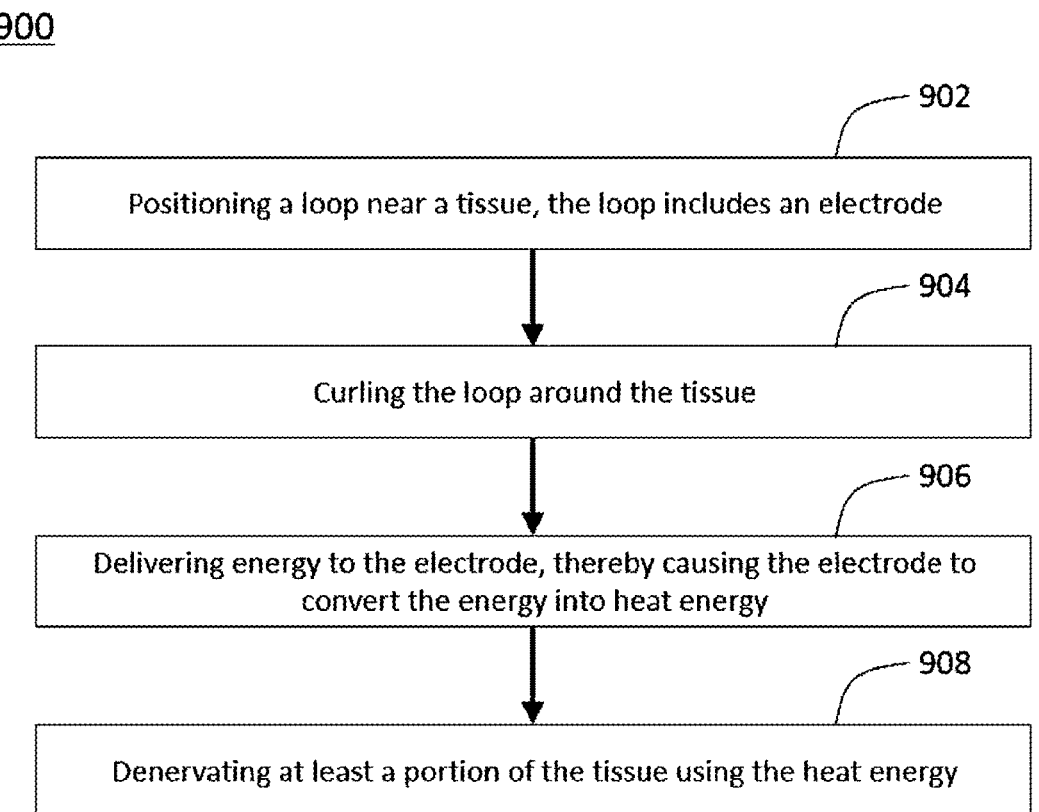
FIG. 9 is a flow chart illustrating exemplary steps that may be carried out to denervate renal nerves according to embodiments of the present invention.

FIG. 9 is a flow chart 900 illustrating exemplary steps that may be carried out to denervate renal nerves according to embodiments of the present invention. The process starts at step 902. At step 902, the loop 20 (or 420) that is positioned near a target tissue, such as circumferential tissue 5 of the renal artery RA. In embodiments, the loop (or 420) may include one or more electrode 23 (or 423). Next, at step 904, the loop 20 (or 420) may be curled around the target tissue.

At step 906, energy may be delivered to the electrode 23, where the electrode 23 may convert the energy into heat energy. Then, at step 908, at least a portion of the target tissue may be denervated by the heat energy.

Figure 10:
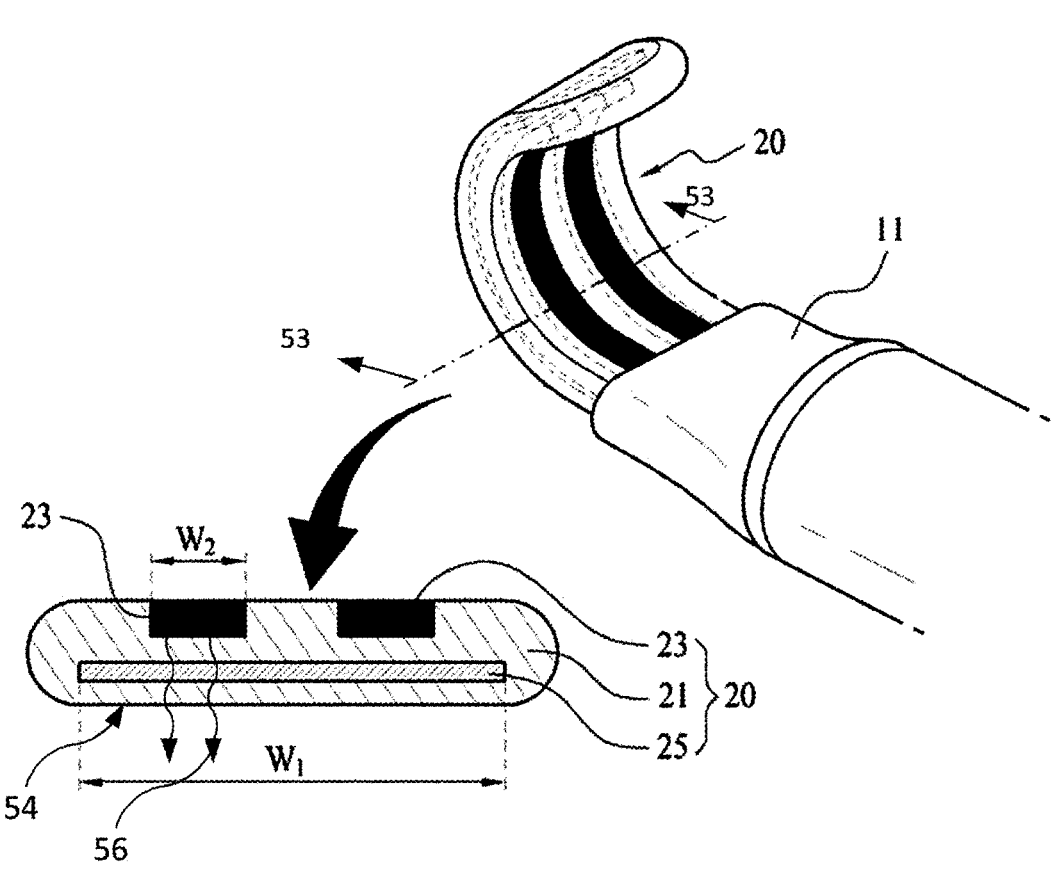
FIG. 10 is a perspective view of a distal end portion of the catheter in FIG. 4 according to embodiments of the present invention.

FIG. 10 is a perspective view of a distal end portion of the catheter in FIG. 4 according to embodiments of the present invention. FIG. 10 also includes a cross sectional view of the loop, taken along the line 53-53, according to embodiments of the present invention.

As depicted, the loop 20 includes a body 21, one or more electrodes 23 disposed on a surface of the body 21 and a substrate 25 embedded in the body 21 and separated from the electrodes 23 by a certain distance.

The body 21 may be made of insulating/elastic materials, such as silicon. The electrodes 23 may extend along the longitudinal direction of the body 21 and may be made of shape-memory alloy, such as Nitinol. The substrate 25 may also extend along the longitudinal direction of the body 21 like the electrodes 23 and may be made of the same material as the electrode. The substrate 25 may be electrically insulated from the electrodes 23. In embodiments, the substrate 25 may be electrically coupled to the energy source generator 205 via a switch (not shown) and may receive electrical energy from the energy source generator 205.

If the substrate 25 is not included in the body 21, a portion of the heat energy generated by the electrode 23 may be transferred toward the backside surface 54 of the body 21, as indicated by the arrows 56. The substrate 25 may prevent the heat energy 56 from being transferred to a tissue on the backside surface 54 of the body 21 while most of the heat energy generated by the electrodes is transferred to the target tissue on the front side surface of the body 21. As a result, the thermal efficiency of the loop 20 may be increased.

The substrate 25 may have a width W1 wider than the width W2 of each of the electrodes 23 to more efficiently prevent energy transfer to the tissue that is on the backside surface 54 of the body 21.

In embodiments, the backside surface 54 of the body 21 may be coated with a thermally insulating material to block a transfer of the heat energy 56.

Figure 11A:
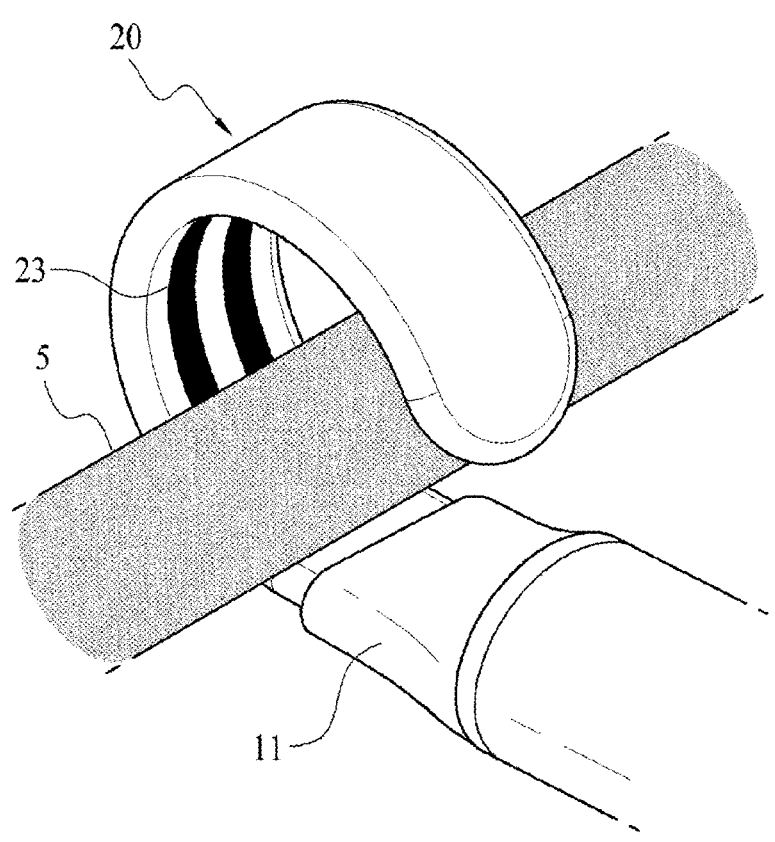
FIG. 11A and FIG. 11B show the loop in FIG. 10 at two different temperatures according to embodiments of the present invention.
Figure 11B:
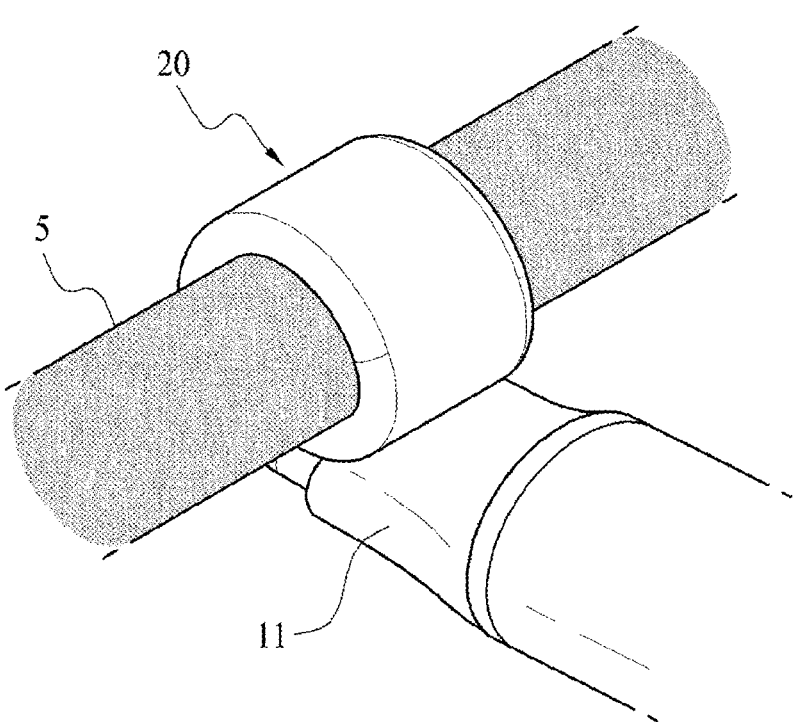

FIG. 11A and FIG. 11B show the loop in FIG. 10 at two different temperatures according to embodiments of the present invention.

Referring to FIG. 11A, the loop 20 curls around the circumferential tissue 5 (e.g., renal artery) as the tip of the loop 20 proceed from the position 60 toward the position 64 as depicted in FIG. 6A to 6D. In other words, the operator may mechanically manipulate the loop control 90 to curl the loop 20 around the circumferential tissue 5 regardless of the temperature of the loop 20. In some cases, the electrodes may firmly contact the circumferential tissue when the loop curls around the circumferential tissue by the operator's manipulation. In other cases, the electrodes of the curled loop may not firmly contact the circumferential tissue for various reasons, such as reduction in the mechanical elasticity of the loop due to the mechanical fatigue developed by repeated usage of the loop 20, reduction in the mechanical force to tighten the loop and so on.

Referring to FIG. 11B, the electrodes and/or the substrate may be made of shape-memory alloy whose shape changes at a critical temperature. In embodiments, as described in conjunction with FIG. 12, the electrodes 23 (or substrate 25) made of the shape-memory alloy may be curved at a first curvature at a low temperature (i.e., below the critical temperature) and return to its pre-deformed shape (i.e., curved at a second curvature) when heated above the critical temperature so that the loop 20 curls tightly around the circumferential tissue 5. For example, the critical temperature may range between 35° C. and 45° C.; preferably, the critical temperature point may be the body temperature of the patient.

As discussed above, the energy delivered to the electrodes 23 or substrate 25 may include one or more of radio-frequency (RF) energy, electrical energy, laser energy, ultrasonic energy, high-intensity focused ultrasound (HIFU) energy, cryogenic energy, and thermal energy. The critical temperature of the shape-memory alloy that the electrodes 23 (or substrate 25) is made of may be reached in two ways. The first way may be that the critical temperature is reached by the energy delivered to the electrodes 23 and the second way may be that the critical temperature is reached by the energy delivered to the substrate 23. More specifically, in the case of the first way, the energy is delivered to the electrodes 23, causing the temperature of the electrodes to rise due to the heat energy generated by the electrodes 23. Also, a portion of the heat energy is transferred to the substrate 25, causing the temperature of the substrate 25 to rise to the critical temperature. As the temperature of the substrate 25 reaches the critical temperature, the substrate 25 may curl more tightly around the target tissue as the shape-memory alloy of the substrate 25 may return to the pre-deformed state. The loop 20 including the substrate 25 may curl more tightly around the target tissue so that the electrodes 23 included to the loop may firmly contact the circumferential tissue, as depicted in FIG. 11B. In the case of the second way, the energy is directly delivered to the substrate 25 so that the temperature of the substrate 25 rises due to the heat energy generated by the substrate. As the temperature of the substrate 25 reaches the critical temperature, the substrate 25 may curl more tightly around the target tissue as the shape-memory alloy of the substrate 25 returns to the pre-deformed state. The loop 20 including the substrate 25 may curl tightly around the target tissue so that the electrodes 23 included to the loop 20 may firmly contact the circumferential tissue, as depicted in FIG. 11B.

As described above, the electrodes 23 may firmly contact the circumferential tissue by either of the two ways, and as a consequence, the renal denervation may be performed more efficiently.

Figure 12:
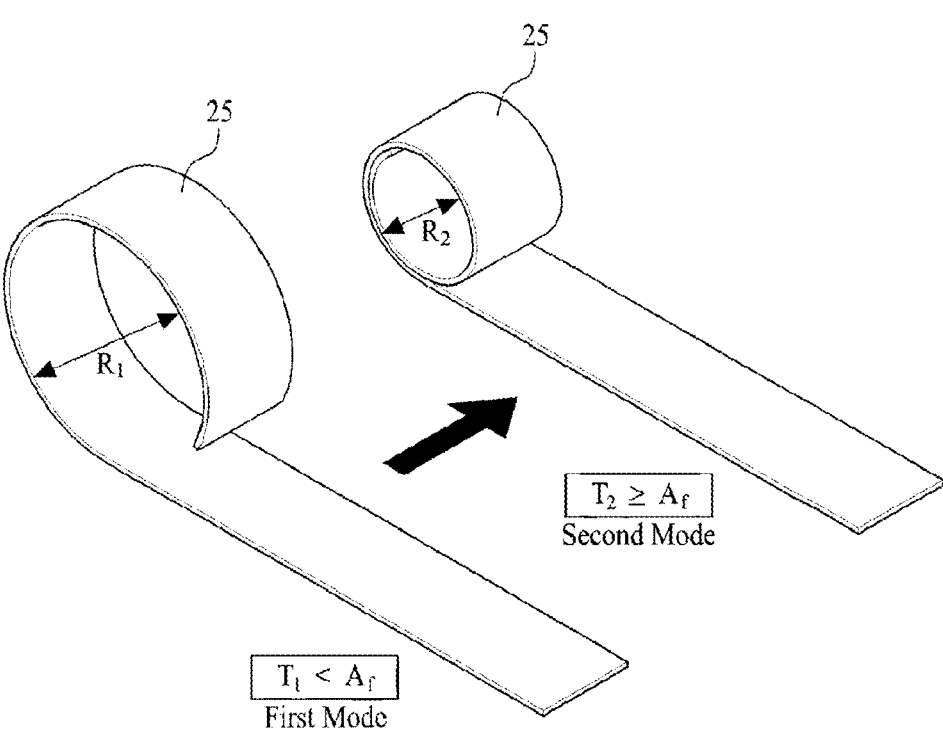
FIG. 12 shows a deformation of the substrate in response to a temperature change according to embodiments of the present invention.

FIG. 12 shows a deformation of the substrate 25 in FIG. 10 in response to a temperature change according to embodiments of the present invention.

As depicted in FIG. 12, at least a portion of the flat substrate is formed of shape-memory alloy and is deformed to different loops depending on its own temperature. In the first mode, when the temperature (T1) of the substrate 25 is less than the critical temperature (Af) (i.e., no energy is delivered to the electrodes 23 or the substrate 25), a portion of the substrate 25 may be curled by manipulating the loop control 90. At this time, the first circular loop of the substrate 25 may be formed by a mechanical bending force that may be applied by the operator's manipulation, where the first diameter (R1) of the first circular loop is large enough to curl around the tissue. In embodiments, the first circular loop of the substrate 25 may be formed by delivering the energy to the electrodes 23 or the substrate 25 while the temperature of the substrate 25 is below the critical temperature.

In the second mode, as shown in FIG. 12, when the temperature (T2) of the substrate 25 reaches the critical temperature (Af) by delivering the energy to the electrodes or the substrate 25, a second circular loop of the substrate 25 may be formed, where the second diameter (R2) of the second circular loop may be smaller than the first diameter (R1). The shape-memory alloy of the substrate 25 may be pre-deformed such that the second diameter (R2) is slightly larger than the circumferential tissue and the electrodes 23 firmly contact the circumferential tissue in the second mode.

In embodiments, the substrate may be made of two-way shape memory alloy but may be made of three-way (or higher order) shape-memory alloy, depending on the application. For instance, the substrate may be made of three-way shape-memory alloy and pre-deformed so that the substrate has return to three shapes at three different temperatures.

Figure 13:
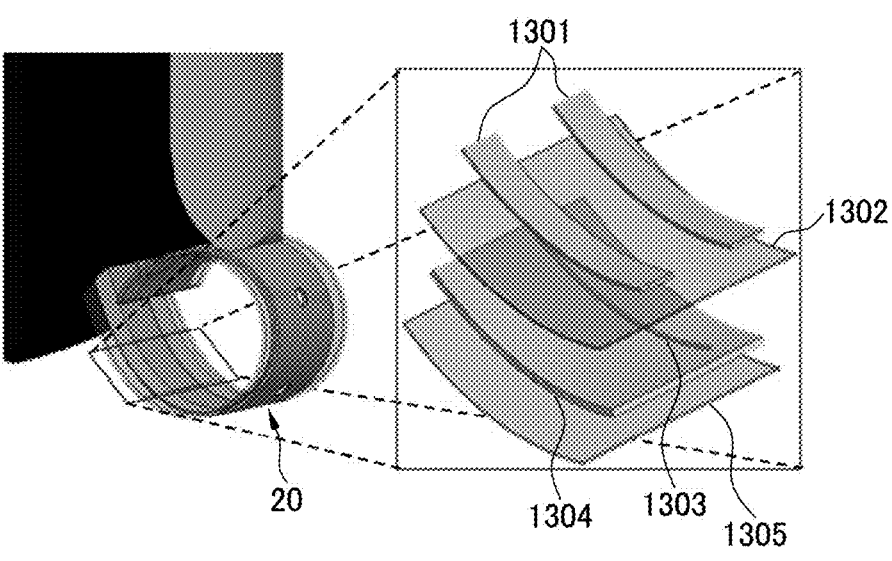
FIG. 13 illustrate a loop of the catheter in FIG. 4 according to embodiments of the present invention.

FIG. 13 illustrate a loop of the catheter in FIG. 4 according to another embodiment of the present invention. The loop may be able to automatically wrap both the tissue and nerves for effective denervation regardless of the nerve distribution. The loop may be available in various sizes to cover main artery, accessory artery, and early-branching artery.

According to the present disclosure, it is possible to effectively ablate e.g., renal nerves while not being as invasive as sympathectomy to treat the resistant hypertension patients. Further, by a procedure using the catheter, the nerves could safely and completely denervated.

As depicted in FIG. 13, the loop may include a plurality of electrodes 1301, a first film 1302, a sensor 1303, a second film 1304 and a third film 1305.

The first film 1302 may be capable of bending to curl around the tissue. The first film 1302 may be disposed on the second film 1304. The first film 1302 may be made of biocompatible polymers. For example, the first film 1302 may be a polyimide film.

The plurality of electrodes 1301 may be disposed on the first film 1302 and arranged in parallel to each other with a predetermined distance. The plurality of electrodes 1301 may contact the circumferential tissue when the loop curls around the circumferential tissue.

The plurality of electrodes 1301 may be formed of electrically-conductive elastic material so that they can deform along with the body as the body is curled/uncurled.

By way of example, the plurality of electrodes 1301 may be made of a copper-coated-gold.

Since the plurality of electrodes 1301 are arranged in parallel to each other, the plurality of electrodes 1301 may form a bipolar configuration localizing electrical current path (e.g., thermal energy) between the plurality of electrodes 1301, and the concentration results in heat generation at tissue. This configuration confines heat between surface of the plurality of electrodes 1301 and an outer wall of the tissue.

The plurality of electrodes 1301 may be configured to curl to directly or indirectly contact the tissue. The plurality of electrodes 1301 may contact the circumferential tissue surrounding the outer surface of the renal artery and generate heat energy when electrical energy, such as RF energy, is supplied, where the heat energy may be used to denervate the renal nerve RN.

In some cases, the plurality of electrodes 1301 may firmly contact the circumferential tissue when the loop curls around the circumferential tissue by the operator's manipulation. In other cases, The plurality of electrodes 1301 of the curled loop may not firmly contact the circumferential tissue for various reasons, such as reduction in the mechanical elasticity of the loop due to the mechanical fatigue developed by repeated usage of the loop, reduction in the mechanical force to tighten the loop and so on.

The plurality of electrodes 1301 may made of the shape-memory alloy may be curved at a first curvature at a low temperature (i.e., below the critical temperature) and return to its pre-deformed shape (i.e., curved at a second curvature) when heated above the critical temperature so that the loop curls tightly around the circumferential tissue. For example, the critical temperature may range between 35° C. and 45° C.; preferably, the critical temperature point may be the body temperature of the patient.

The critical temperature of the shape-memory alloy that the plurality of electrodes 1301 may be made of may be reached in two ways. The critical temperature is reached by the energy delivered to the plurality of electrodes 1301. More specifically, the energy is delivered to the plurality of electrodes 1301, causing the temperature of the electrodes to rise due to the heat energy generated by the plurality of electrodes 1301. Also, a portion of the heat energy is transferred to the entire loop, causing the temperature of the loop to rise to the critical temperature. As the temperature of the loop reaches the critical temperature, the loop may curl more tightly around the target tissue as the shape-memory alloy of the plurality of electrodes 1301 may return to the pre-deformed state. Thus, the loop may curl more tightly around the target tissue so that the plurality of electrodes 1301 included to the loop may firmly contact the circumferential tissue.

In the first mode, when the temperature (T1) of the loop is less than the critical temperature (Af) (i.e., no energy is delivered to the plurality of electrodes 1301), a portion of the loop may be curled by manipulating the loop control. At this time, the first circular loop of the loop may be formed by a mechanical bending force that may be applied by the operator's manipulation, where the first diameter (R1) of the first circular loop is large enough to curl around the tissue. In embodiments, the first circular loop of the loop may be formed by delivering the energy to the plurality of electrodes 1301 while the temperature of loop is below the critical temperature.

In the second mode, when the temperature (T2) of the loop reaches the critical temperature (Af) by delivering the energy to the electrodes or the plurality of electrodes 1301, a second circular loop of loop may be formed, where the second diameter (R2) of the second circular loop may be smaller than the first diameter (R1). The shape-memory alloy of the plurality of electrodes 1301 may be pre-deformed such that the second diameter (R2) is slightly larger than the circumferential tissue and the plurality of electrodes 1301 firmly contact the circumferential tissue in the second mode.

Meanwhile, increasing an energy to reach beyond 2 mm would cause irreversible intima injury resulting in serious complications such as atherosclerosis, thrombosis, or stenosis.

To solve the problem, the plurality of electrodes 1301 may localize heat distribution between the plurality of electrodes 1301 and the outer wall of the tissue. Therefore, since thermal damage to tunica intima is prevented by concentrating the heat between the plurality of electrodes 1301 and the outer wall of the tissue, it is possible to achieve the nerve denervation without injuring the tissue and its adjacent organs. Further, it is possible to maximize nerve denervation by localizing the heat distribution within the nerves and thus neural density can be decreased enough.

For example, a temperature of the loop may remain 60° C. to form a thermal lesion boundary between tunica media and adventitia or the temperature of the loop may remain 65° C. to extend the lesion boundary to the tunica media.

The plurality of electrodes 1301 may be configured to supply bipolar energy. The energy supplied by the plurality of electrodes 1301 may be at least one selected from the group consisting of radio-frequency (RF) energy, electrical energy, laser energy, ultrasonic energy, high-intensity focused ultrasound (HIFU) energy, cryogenic energy, thermal energy The plurality of electrodes 1301 may include a first electrode to deliver thermal energy to a first treatment zone of the tissue and a second electrode to deliver thermal energy to a second treatment zone of the tissue. Thermal energy delivered to the plurality of electrodes 1301 is localized between the first treatment zone and the second treatment zone.

The sensor 1303 may be disposed on the second film 1304. The sensor 1303 may be disposed at a position corresponding to a position between the plurality of electrodes 1301. The sensor 1303 may be electrically insulated from the plurality of electrodes 1301. The sensor 1303 may sense at least one of an impedance of the plurality of electrodes 1301 and a temperature of the tissue.

The second film 1304 may be disposed on the third film 1305. The second film 1304 may be made of biocompatible metals. By way of example, the second film 1304 may be a biocompatible heat-treated stainless steel plate that changes shape from straight to round when emerged from the distal portion, and it maintains its round shape without external load. The second film 1304 may be coated with a flexible printed circuit board.

The third film 1305 may also be made of biocompatible polymers. For example, the third film 1305 may be a polyimide film.

To achieve complete denervation while preventing damage to the outer wall of the tissue, the applicant analyzed temperature distribution during denervation with thermo-electrical finite element modeling (FEM) using ANSYS Fluent.

The Bio-heat equation is the governing equation to obtain the thermal distribution in the tissue. The equation below describes the coupled electric and thermal problems.

$$\rho c \frac{\partial T}{\partial t} = \nabla \cdot k \nabla T + q - Q_{cooling} + Q_{meta}$$

Where T is temperature, t is time, and other parameters are thermal properties: thermal conductivity of tissue k, the specific heat of tissue c, and mass density of tissue p; electrical properties: heat source from electrical energy q; and temperature cooling effect caused by blood or airflow $Q_{cooling}$. In this simulation, the metabolic heat $Q_{meta}$ is ignored since it is negligible compared to others.

With respect to the electric problem, the 1 MHz wavelength of the signal used in this simulation is more than the size of the plurality of electrodes 1301 wrapping the renal artery and nerves. Therefore a quasi-static approximation was applied to solve the electric fields in the renal artery and nerves. A governing equation used to solve electrical potential in the tissue is given by:

$$V \cdot \sigma \nabla V = 0$$

Where a is the electrical conductivity of the tissue, and V is electrical potential. The electric field is the gradient of electrical potential.

$$E = -\nabla V$$

The heat source term q was calculated using Ohm's law.

$$q = J \cdot E = \sigma (\nabla V)^2$$

The electrical conductivity of the tissue is temperature-dependent and is as given by:

$$\sigma(T) = \sigma_0 (1 + k \Delta T)$$

Where σ is electrical conductivity, $\sigma_0$ is reference electrical conductivity at 25° C., k is the temperature constant, and ΔT is the temperature difference from 25° C. We set the temperature constant at 2%° C.-1.

A convection effect was applied at the outer arterial wall as a boundary condition:

$$Q_{air} = h(T - T_0)$$

Here, free convection at walls exposed to $CO_2$ gas with convective heat transfer coefficient (h) of 25 Wm-2K-1 and free stream temperature (To) of 300 K are assumed.

In renal denervation, due to the detachment of target renal artery from fat, periarterial connective tissue and capillaries, the blood perfusion in the artery will be decreased. In addition, the cooling effect by bulk blood flow in this detached artery is more dominant than blood perfusion. Therefore, fluid flow is used to simulate blood cooling effect and not blood perfusion in the lumen of the artery. Blood cooling effect (Qblood) was simulated using a velocity inlet (blood flow rate) and a static pressure outlet as 0 Pa. In ANSYS Fluent, the Bio-heat equation was coded and applied to model via a built-in user-defined function. Using the user-defined scalar and the specified value at both electrodes, with zero specified flux at the other parts, the transient situation with 1 second time step size and 90-time steps in in vitro stimulation and the steady-state situation in vivo simulation is simulated.

After establishing a validity of using a meshing method, bio-heat equation, and setting boundary conditions in vitro, the applicant extended these techniques to in-vivo simulation with the renal artery model. In in-vivo simulation, the artery 3D was designed based on previous histological studies where the diameter of the artery, the diameter of the lumen, and thickness of the artery wall were 5 mm, 2 mm, and 1.5 mm, respectively. The arterial wall was composed of tunica media and adventitia. To analyze the heat distribution in various in-vivo simulations, the ratio of the thickness of the tunica media and adventitia was changed while maintaining the total diameter of the artery as 5 mm. Compared to a phantom gel in in-vitro modeling, in in vivo arterial blood flow was taken into account with the flow rates from 0.28 to 0.68 m/s. The blood temperature was set as 310 K with other conditions remaining the same. At electrode-tissue interfaces, the electric potential of an electrode was zero. The electric potential of the other electrode was chosen to make the temperature between the two electrodes at 60 or 65° C. in the steady-state condition. The modeling domain was a cuboid with 30 mm (height)×20 mm (length)×20 mm (width) in the phantom simulation. The artery was of the cylinder in shape with a height of 20 mm and a radius of 2.5 mm in vivo simulation. The default element size was 0.1 mm, and the element size near the electrodes was 0.05 mm.

Here, the phantom was manufactured by mixing 6 L water with 48 g gelling agent (polyacrylic acid solution, Sigma-Aldrich) in a 160 mm×430 mm×170 mm acrylic water tank. In this phantom gel, we considered that the convection effect was almost zero, mass density and specific heat were the same with water. The electrical conductivity of the phantom was measured using an impedance analyzer (E4990A, Keysight Technologies).

Figure 14A:
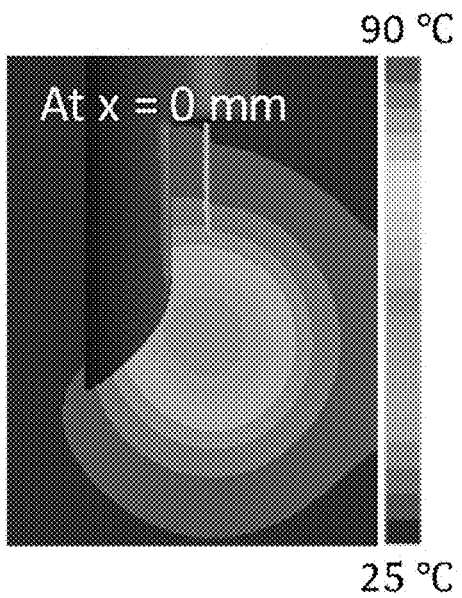
FIG. 14A and FIG. 14B show thermal distribution in the cross section of the loop a finite element modeling and FIG. 14C shows a scatter plot of temperature normalized by a sensor showing the difference between a simulation and experimental results.
Figure 14B:
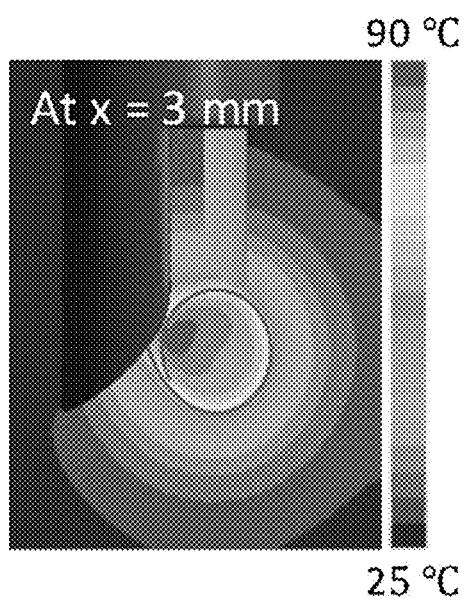
Figure 14C:
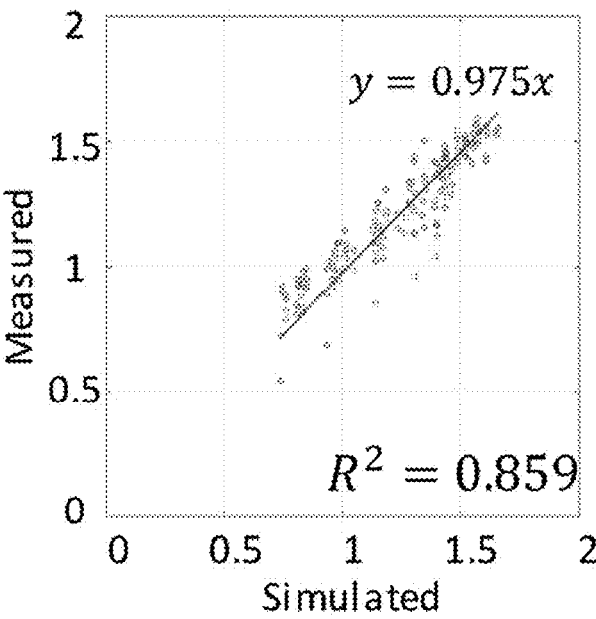

FIGS. 14A and 14B show the heat distribution at x=0 and x=3 planes in the FEM model of the parameter-controlling phantom gel after heating 90 seconds. The simulated peak temperature distribution in x=3 plane is higher than the temperature in x=0 plane. The results confirm that the catheter apparatus could focus heat inside the loop and between parallel electrodes. This simulation model was validated by comparing the simulated temperature profiles with experimental results at a total of 169 points (13 points for each 13 section planes). The temperature at the center of the loop is measured at 14 points, 13 points are for fiber optic temperature probe, and the final point is for the sensor e.g., thermocouple probes integrated within the loop. The simulation and experimental results of normalized temperatures measured by the sensor in simulation and experiment are shown in FIG. 14C using scatter plots. The coefficient of determination in the scatter is 0.859, and the overall average error is 6.97%. The effect of the thermal conductivity from the sensitivity analyses shows that the peak temperature did not differ more than 1.2° C. between simulations and experimental methods, which is an acceptable difference. This good agreement between the simulation study and validation experiments confirmed the credibility of the simulation method and modeling.

Figure 15A:
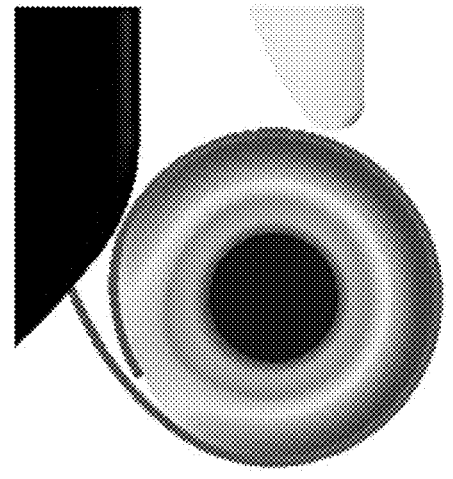
FIG. 15A shows thermal distribution at the cross section of 3D artery model and FIG. 15B shows thermal distribution at the longitudinal section of the 3D artery model.
Figure 15B:
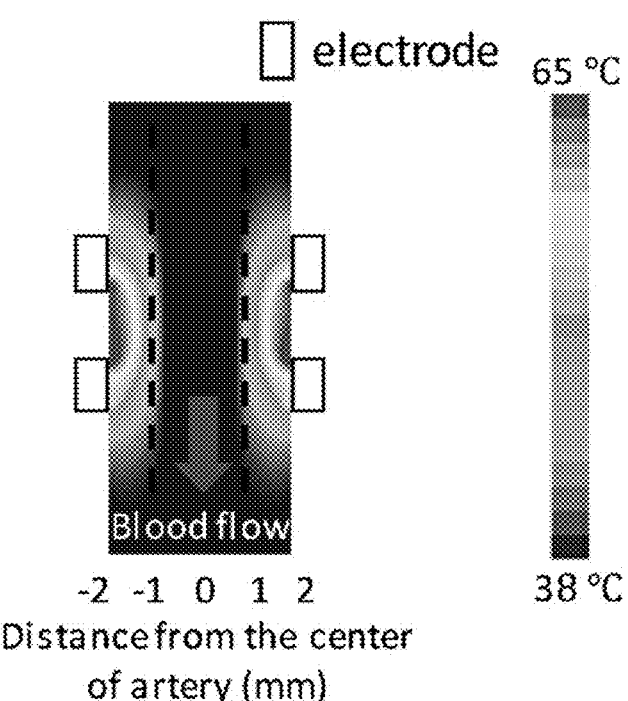

The applicant further utilized a numerical simulation model to evaluate the thermal distribution at the loop of the artery 3D model. The model's artery length, lumen diameter, the thickness of tunica media, and adventitia were set to 20 mm, 2 mm, 0.6 mm, and 0.9 mm respectively, with the blood flow rate set to 0.68 m/s. With the temperature of the loop maintained at 65° C., the peak temperature distribution at the cross-section and the longitudinal section of the 3D artery model are shown in FIGS. 15A and 15B. The heat is concentrated on the outside of the artery, in the cross-section, and between the parallel electrodes in the longitudinal section. The temperature profiles at the center of two parallel electrodes are shown in FIG. 16.

As an isothermal line, which is the thermal lesion boundary, or a nonviable volume, 50° C. was set. Typically the renal nerves are distributed in tunica adventitia and periarterial connective tissue. Therefore, the ideal thermal lesion boundary should be located in the border between tunica media and adventitia while preventing thermal damage to tunica intima or lumen.

Figure 16:
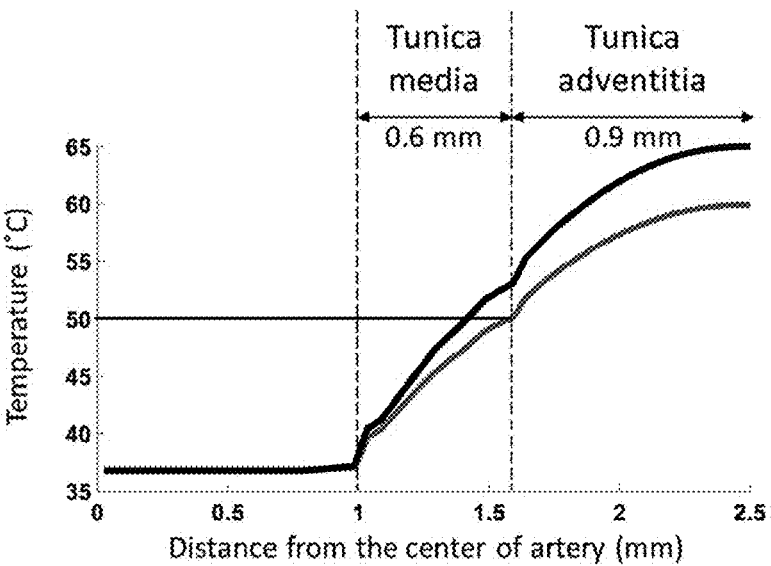
FIG. 16 shows two-dimensional temperature profiles.

FIG. 16 shows the border as a black dashed line at x=1.6 mm. When the temperature of the loop remained at 60° C., the thermal lesion boundary was formed between tunica media and adventitia. As the temperature of the loop reached 65° C., the lesion boundary extended to the tunica media.

The apparatus described herein can be used to treat not only hypertension, but also other suitable types of diseases, such as chronic renal diseases, cardiovascular disorders, cardiac arrhythmias, and clinical syndromes where the renal afferent activation is involved. Using the catheter in embodiments, as compared to percutaneous catheter and surgical instrumentation, the physician may treat the diseases in an easier and safer manner.

In the description, numerous details are set forth for purposes of explanation in order to provide a thorough understanding of the present invention. However, it will be apparent to one skilled in the art that not all of these specific details are required in order to practice the present invention.

Additionally, while specific embodiments have been illustrated and described in this specification, those of ordinary skill in the art appreciate that any arrangement that is calculated to achieve the same purpose may be substituted for the specific embodiments disclosed. This disclosure is intended to cover any and all adaptations or variations of the present invention, and it is to be understood that the terms used in the following claims should not be construed to limit the invention to the specific embodiments disclosed in the specification. Rather, the scope of the invention is to be determined entirely by the following claims, which are to be construed in accordance with the established doctrines of claim interpretation, along with the full range of equivalents to which such claims are entitled.

What is claimed is:

1. A catheter apparatus for perivascular nerve denervation, comprising:

a shaft having a distal end; and a loop disposed near the distal end and configured to curl so as to contact a tissue and receive, via the shaft, energy to denervate at least a portion of the tissue, wherein the loop is configured to curl onto itself as the loop emerges distally from the distal end of the shaft and includes: a first film capable of bending to curl around the tissue;

a plurality of electrodes disposed on the first film and arranged in parallel to each other with a predetermined distance and configured to curl to directly contact the tissue; and a sensor disposed at a position corresponding to a position between the plurality of electrodes, and wherein the plurality of electrodes includes a first electrode extending along a direction in which the loop is configured to emerge from the shaft, the first electrode configured to deliver thermal energy to a first treatment zone of the tissue, and a second electrode extending along the direction in which the loop is configured to emerge from the shaft, the second electrode configured to deliver thermal energy to a second treatment zone of the tissue, and wherein when the energy is received by the first electrode and the second electrode, the first electrode and the second electrode localize heat distribution between the first electrode and the second electrode so that the thermal energy delivered by the first electrode to the first treatment zone and the thermal energy delivered by the second electrode to the second treatment zone is localized between the first treatment zone and the second treatment zone.

2. The catheter apparatus of claim 1, wherein the plurality of electrodes are is configured to form a bipolar configuration to localize the thermal energy delivered by the first electrode to the first treatment zone and the thermal energy delivered by the second electrode to the second treatment zone.

3. The catheter apparatus of claim 1, wherein the loop further includes a second film on which the first film is disposed.

4. The catheter apparatus of claim 3, wherein the sensor is disposed on the second film.

5. The catheter apparatus of claim 3, wherein the first film is a polyimide film, and the second film is a biocompatible heat-treated stainless steel plate.

6. The catheter apparatus of claim 3, wherein the loop further includes a third film on which the second film is disposed.

7. The catheter apparatus of claim 1, wherein the energy received by the loop is at least one selected from the group consisting of radio-frequency (RF) energy and electrical energy.

8. The catheter apparatus of claim 1, wherein the sensor is electrically insulated from the plurality of electrodes and is configured to sense at least one of an impedance of the plurality of electrodes or a temperature of the tissue.

9. The catheter apparatus of claim 1, wherein the tissue includes at least one of a nerve, lymphatics, or capillaries around an artery.

10. A method for perivascular nerve denervation using a catheter apparatus, the catheter apparatus comprising a shaft having a distal end and a loop disposed near the distal end and configured to curl so as to contact a tissue and receive, via the shaft, energy to denervate at least a portion of the tissue, wherein the loop is configured to curl onto itself as the loop emerges distally from the distal end of the shaft and includes a first film capable of bending to curl around the tissue, a plurality of electrodes disposed on the first film and arranged in parallel to each other with a predetermined distance and configured to curl to directly contact the tissue and a sensor disposed at a position corresponding to a position between the plurality of electrodes, wherein the plurality of electrodes includes a first electrode extending along a direction in which the loop is configured to emerge from the shaft, the first electrode configured to deliver thermal energy to a first treatment zone of the tissue, and a second electrode extending along the direction in which the loop is configured to emerge from the shaft, the second electrode configured to deliver thermal energy to a second treatment zone of the tissue, and wherein when the energy is received by the first electrode and the second electrode, the first electrode and the second electrode localize heat distribution between the first electrode and the second electrode so that the thermal energy delivered by the first electrode to the first treatment zone and the thermal energy delivered by the second electrode to the second treatment zone is localized between the first treatment zone and the second treatment zone, and the method comprises:

positioning the loop near the tissue, delivering the energy to the plurality of electrodes, thereby to cause the loop to curl around the tissue;

causing the plurality of electrodes to convert the energy into the thermal energy delivered to the first treatment zone and the thermal energy delivered to the second treatment zone; and denervating at least the portion of the tissue using the thermal energy delivered to the first treatment zone and the thermal energy delivered to the second treatment zone.

11. The method of claim 10, wherein the plurality of electrodes are configured to form a bipolar configuration to localize the thermal energy delivered by the first electrode to the first treatment zone and the thermal energy delivered by the second electrode to the second treatment zone 2-3.

12. The method of claim 10, wherein the tissue includes at least one of a nerve, lymphatics or capillaries around an artery.

13. The method of claim 10, further comprising:

sensing an impedance of the plurality of electrodes or a temperature of the tissue through the sensor.

* * * * *